(12) United States Patent
Bergfjord

(10) Patent No.: US 7,796,728 B2
(45) Date of Patent: Sep. 14, 2010

(54) X-RAY APPARATUS

(75) Inventor: Per Harald Bergfjord, Middlesex (GB)

(73) Assignee: Elekta AB (publ), Stockholm (SE)

( * ) Notice: Subject to any disclaimer, the term of this patent is extended or adjusted under 35 U.S.C. 154(b) by 286 days.

(21) Appl. No.: 11/659,243

(22) PCT Filed: Jul. 25, 2005

(86) PCT No.: PCT/GB2005/002894
§ 371 (c)(1),
(2), (4) Date: Aug. 20, 2008

(87) PCT Pub. No.: WO2006/013325
PCT Pub. Date: Feb. 9, 2006

(65) Prior Publication Data
US 2009/0213990 A1    Aug. 27, 2009

(30) Foreign Application Priority Data
Aug. 5, 2004    (GB) ................... 0417399.3

(51) Int. Cl.
*A61N 5/10* (2006.01)
*G21K 1/04* (2006.01)
(52) U.S. Cl. ........................ 378/65; 378/150
(58) Field of Classification Search ............ 378/4, 378/15, 19, 65, 62, 64, 150
See application file for complete search history.

(56) References Cited

U.S. PATENT DOCUMENTS

| | | | |
|---|---|---|---|
| 5,822,395 A | 10/1998 | Schardt et al. | 378/137 |
| 6,842,502 B2 * | 1/2005 | Jaffray et al. | 378/65 |
| 2003/0043966 A1 | 3/2003 | Blin et al. | 378/138 |
| 2003/0076927 A1 | 4/2003 | Nakashima et al. | 378/65 |
| 2003/0138078 A1 | 7/2003 | Eberhard et al. | 378/145 |

FOREIGN PATENT DOCUMENTS

| | | |
|---|---|---|
| EP | 0994428 A2 | 4/2000 |
| WO | WO 00/62674 | 10/2000 |
| WO | WO 03/081220 | 10/2003 |
| WO | WO 2004/075118 | 9/2004 |

* cited by examiner

*Primary Examiner*—Irakli Kiknadze
(74) *Attorney, Agent, or Firm*—Z. Peter Sawicki; Westman, Champlin & Kelly, P.A.

(57) ABSTRACT

An investigative X-ray apparatus comprises a source of X-rays emitting a cone beam centred on a beam axis, a collimator to limit the extent of the beam, and a two-dimensional detector, the apparatus being mounted on a support which is rotatable about a rotation axis, the collimator having a first state in which the collimated beam is directed towards the rotation axis and the second state in which the collimated beam is offset from the rotation axis, the two-dimensional detector being movable accordingly, the beam axis being offset from the rotation axis by a lesser amount than the collimated beam in the second state. The X-ray source is no longer directed towards the isocentre as would normally be the case; the X-ray source is not orthogonal to the collimators. This is advantageous in that the entire field of the X-ray tube can be utilised. As a result, a lesser field is required of the X-ray tube and the choice of tube designs and capacities can be widened so as to optimise the performance of the X-ray tube in other aspects.

13 Claims, 5 Drawing Sheets

X-RAY APPARATUS

CROSS-REFERENCE TO RELATED APPLICATION

This application is a Section 371 National Stage Application of International Application No. PCT/GB2005/002894, filed 25 Jul. 2005 and published as WO 2006/013325 on 9 Feb. 2006, in English.

FIELD OF THE INVENTION

The present invention relates to X-ray apparatus, in particular X-ray apparatus that has an investigative function. Such X-ray apparatus can be stand-alone X-ray apparatus, for purely investigative purposes, or can be integrated as part of an investigative function provided on a radiotherapeutic apparatus.

BACKGROUND ART

Computed Tomography scanning is a well known diagnostic technique and, in Its cone beam form, involves directing a wide beam of X-rays towards and through the patient and capturing the resulting two-dimensional image on a flat panel detector behind the patient. The apparatus (source and detector) is then rotated around the patient to obtain a multiplicity of images from different directions. These images are combined via a suitable computing means in order to produce a three-dimensional representation of the internal structure of the patient.

One limiting factor is the cost and size of the detector. Flat panel X-ray detectors are typically very expensive, and the cost increases with the dimensions of the detector. In practice this places an upper limit on the possible size of the flat panel detector. This in turn places a limit on the maximum aperture of the apparatus.

There are ways to increase the effective aperture of the device, within limits. Normally, the cone beam is directed along a central beam axis that coincides with the isocentre of the device, and the flat panel detector is centred on that beam axis. This will mean that each successive image taken by the flat panel detector will show a section of the patient centred on the isocentre. These can then be reconstructed in the normal way.

However, for particularly large patients this aperture may be insufficient. In this case, the aperture of the apparatus can be increased by moving the flat panel detector such that the central beam axis intersects near to one edge of the detector. This X-ray beam can then be collimated differently so that the cone beam is offset from the (previous) central beam axis and still covers the area of the flat panel detector. The beam will then be centred on an offset beam axis. In this case, each individual image will only show half of the relevant portion of the patient. However, after the apparatus has rotated through 180°, the other half will be brought into the image. When these images are reconstructed using a suitably reconstructed algorithm, a complete rendering of the patient will still be possible, albeit with a lower resolution reflecting the fact that each voxel of the reconstructed volume has been reconstructed using only half the amount of data.

SUMMARY OF THE INVENTION

Whilst this arrangement is potentially beneficial in that it allows a different compromise to be reached between aperture and image quality in cases that demand it, it does place some limitations on the apparatus design. In particular, the X-ray tube must be able to provide a beam that is of twice the width otherwise required. This limits the choice and specification of X-ray tubes that can be used and may impose difficulties in other areas, in that a tube that is able to provide a sufficiently wide beam may be inadequate in other ways.

The present invention therefore provides an investigative X-ray apparatus, comprising a source of X-rays emitting a cone beam centred on a beam axis, a collimator to limit the extent of the beam, and a two-dimensional detector, the apparatus being mounted on a support which is rotatable about a rotation axis, the collimator having a first state in which the collimated beam is directed towards the rotation axis and the second state in which the collimated beam is offset from the rotation axis, the two-dimensional detector being movable accordingly, the beam axis being offset from the rotation axis by a lesser amount than the collimated beam in the second state.

Thus, in effect, the X-ray source is given a permanent offset of a few degrees (such as 3-4°) such that its natural axis is halfway between the two extremes called for by the collimator. The X-ray source is no longer directed towards the isocentre as would normally be the case.

Thus, in an alternative aspect, the present invention provides an investigative X-ray apparatus comprising an X-ray source and a collimator set in which the beam is not orthogonal to the collimators.

This is advantageous in that the entire field of the X-ray tube can be utilised. X-ray tubes typically have edge effects such as tube heel, and this can be kept away from both potential images. As a result, a lesser field is required of the X-ray tube and the choice of tube designs and capacities can be widened so as to optimise the performance of the X-ray tube in other aspects.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
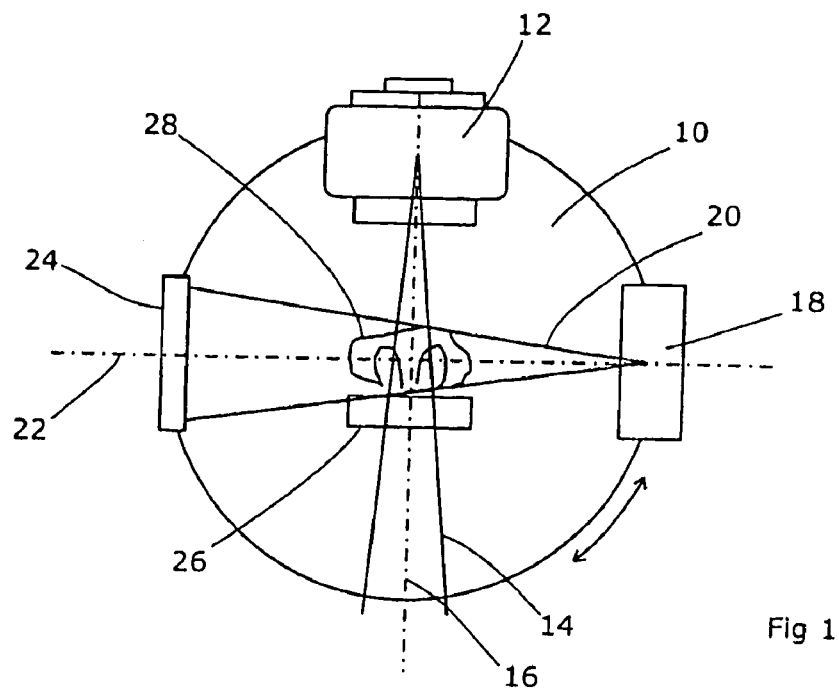
FIGS. 1 and 2 show a conventional machine in normal and offset states, respectively.

FIG. 1 shows a typical radiotherapy machine. This has a rotatable support 10 on which is mounted a therapeutic X-ray source 12 which is able to produce a collimated beam of high energy X-rays 14 centred on a therapeutic beam axis 16. Also mounted on the rotatable support 10 is an investigative X-ray source 18, which produces a beam of low-energy X-rays 20 along an investigative beam axis 22. On the opposite side of the support 10, a flat panel detector 24 is positioned so as to intersect with the investigative beam axis 22.

The rotatable support 10 is arranged to rotate about an axis which passes through the coincidence of the therapeutic beam axis 16 and the investigative beam axis 22, and which is orthogonal to both axes. In this case, the therapeutic beam axis and the investigative beam axis are orthogonal to each other, but this is not essential and other designs are possible. The point of coincidence of the two beam axis 16, 22 and the rotation axis of the support 10 is referred to as the "isocentre". A patient table 26 is located slightly below the isocentre, and a patient 28 resting on the patient table will therefore just lie at the isocentre of the apparatus. In practice, the patient table 26 is made so as to be moveable, to allow the patient to be positioned relative to the isocentre, and permit the treatment of tumours at a variety of bodily locations.

During treatment, the therapeutic X-ray source 12 is activated and the beam 14 is collimated so as to match the shape of the tumour. The rotatable support 10 can be used to rotate the therapeutic X-ray source 12 around the patient so as to direct the beam 14 towards the patient from a variety of directions. Provided that the tumour is at or near the isocentre, it will always be Irradiated. However, the use of a variety of irradiation directions is one factor in reducing the dosage given to healthy tissue whilst maximising the dosage given to the tumour.

It is of course essential to ensure that the patient is correctly positioned prior to treatment. To do so, the investigative X-ray source 18 is activated and the low energy beam 20 is passed through the patient and, after attenuation by the patient, is detected by the flat panel detector 24. This produces a two-dimensional projection image of the patient. The rotatable support 10 is then used to rotate the investigative X-ray source 18 and the flat panel detector 24 around the patient thereby producing a collection of projected images showing the patient from every variety of directions. These can be reconstructed using known algorithms to produce a three-dimensional image of the patients adhering structure, the process known as computed tomography or CT scanning. This internal image of the patient can be used as a final check that the patient is in the correct position, and potentially, as a source of feedback to allow fine adjustment of the position of the patient table 26.

In FIG. 1, the investigative beam 20 is shown collimated so that the image it projects covers the entire working surface of the flat panel detector 24. As a result, the width of the beam 20 at the patient 28 is large enough to ensure that the whole of the patient 28 is included in the image obtained by the flat panel detector 24. Problems can arise in the case of very large patients, part of whom will lie outside the beam 20. In general, it is not possible simply to select a larger flat panel detector 24 and allow a wider beam, since the flat panel detector 24 is a high value item and larger examples cannot be procured at economic cost.

Figure 2:
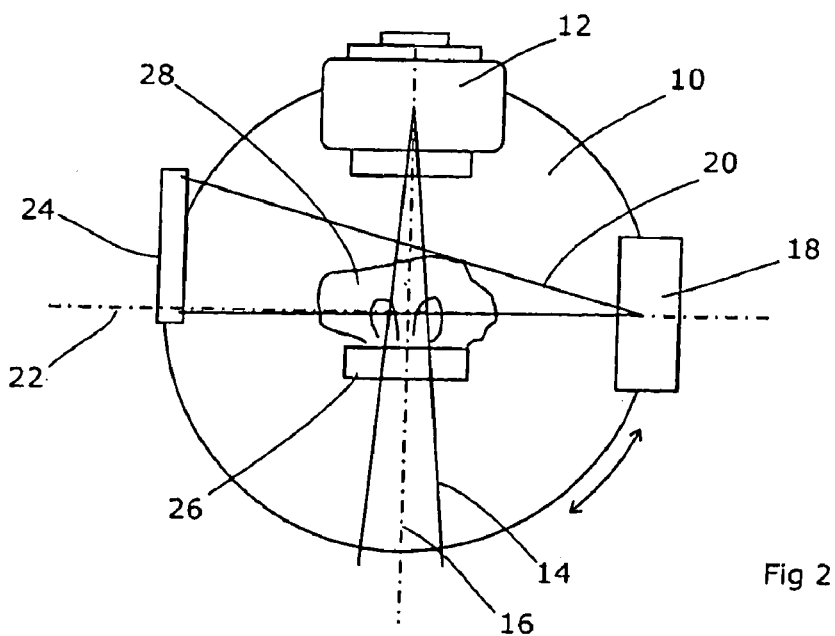

Accordingly, larger patients are dealt with as shown in FIG. 2. The same flat panel detector 24 is moved on its support to an offset position, as shown. Whilst the flat panel detector 24 still coincides with the investigative beam axis 22, that axis 22 now crosses the flat panel detector 24 near one edge of the detector 24. The investigative beam 20 is now collimated slightly differently so that it is no longer centred on the investigative axis 22 but extends from that axis 22 and to one side. As a result, the beam 20 produces an image of approximately one half of the patient 28, in this case the half lying above the isocentre. However, as the apparatus is rotated around the patient 28, after a total rotation of 180° the image will show the area of the patient below the isocentre.

Figure 3:
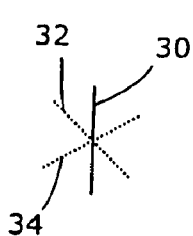
FIGS. 3 and 4 illustrate diagrammatically the field coverage of the normal and offset states, respectively.
Figure 4:
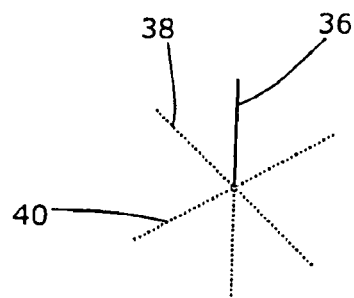

FIGS. 3 and 4 illustrate the point schematically. In FIG. 3, the solid vertical line 30 shows the section of the patient which is being viewed at the start of the rotation process. This is represented as a line, whereas the images are of course projected images rather than a section, but FIG. 3 illustrates the principle only. As the apparatus rotates, the effective image moves through an angle to the dotted line 32, and as rotation continues further the images moves to the dotted line 34. Thus, as rotation continues, the image taken of the patient maps out a cylindrical volume centred on the axis of rotation.

FIG. 4 illustrates the offset method. A solid line 36 of identical length to the solid line 30 is again rotated, but this time the axis of rotation is at one end of the solid line 36. Thus, as the image rotates through 38 and 40 etc., a larger cylinder is mapped out. This caters for the larger patient. However, it can be seen that twice as many lines are required to map out the same cylindrical volume. Thus, the offset rotation arrangement must either spend twice as long gathering images in order to produce the same quality CT reconstruction, or must accept a lower quality CT reconstruction deriving from fewer images. This choice is however clinically useful.

Figure 5:
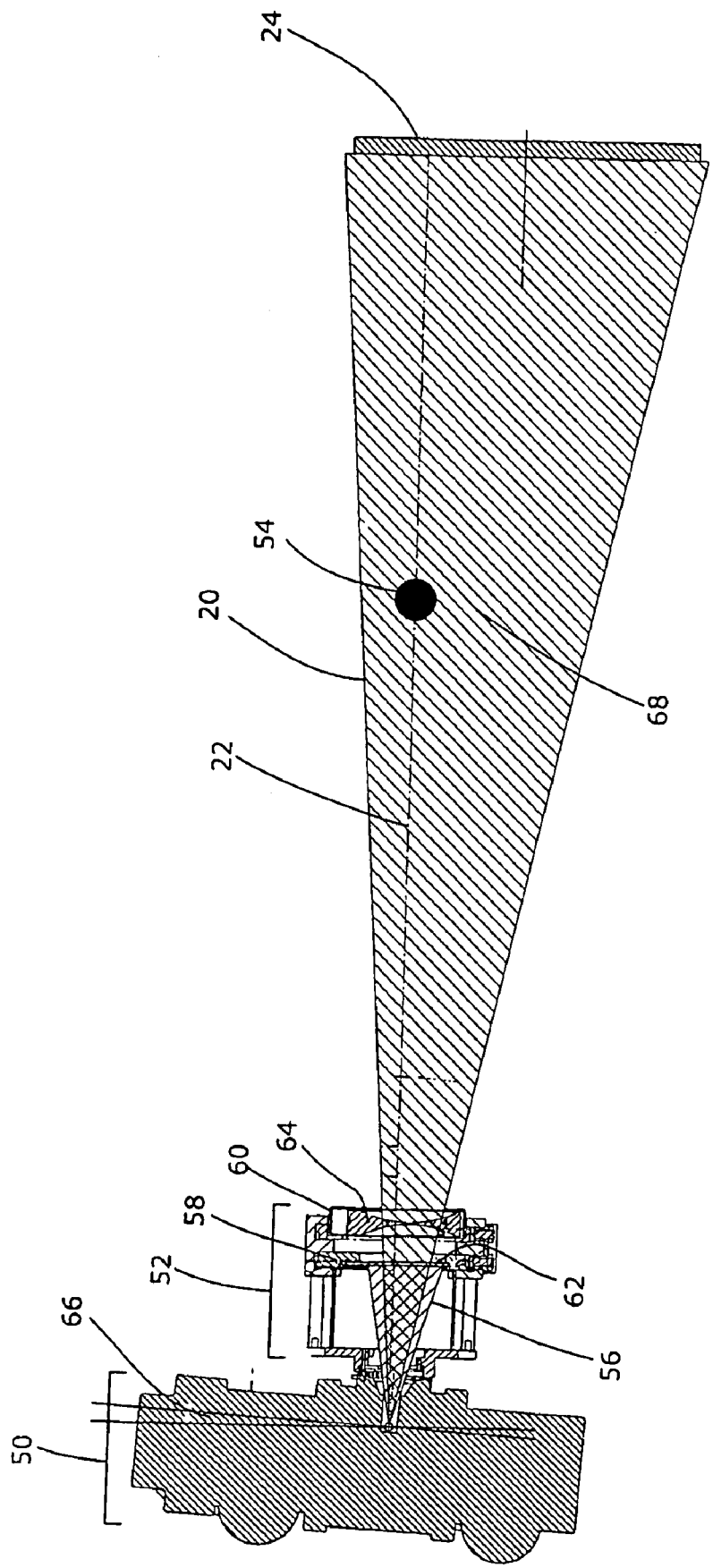
FIG. 5 shows the apparatus according to the present invention in a first collimation.

FIG. 5 shows an improved apparatus for use in this type of diagnosis. This comprises, in general, an X-ray generating source 50 and a collimator set 52. The investigative beam axis 22 is shown, together with the isocentre 54 and the flat panel detector 24.

The X-ray source 50, which we will described in more detail later, produces a beam 56 which is then collimated in the collimator 52. In this design of collimator set 52, a number of slots 58, 60 are provided to receive collimators and filters as required. The first slot 58 contains a beam collimator 62 to produce the investigative beam 20 from the output beam 56 of the source 50, so that the beam 20 just covers the flat panel detector 24. In this case, as shown, the beam collimator 62 collimates the beam 56 evenly, by reducing its width equally on both sides.

As shown in FIG. 5, the collimator 52 is aligned with the beam axis 22 and the isocentre 54. However, the X-ray source 50 is offset by an angle 66 from being perfectly orthogonal to the investigative beam axis 220. As a result, the X-ray source 50 and the collimator 52 are not in alignment, and the approximate centre 68 of the beam does not coincide with the isocentre 54. However, the beam does extend across the beam axis 22 and the isocentre 58 is included within the extent of the beam 20.

Figure 6:
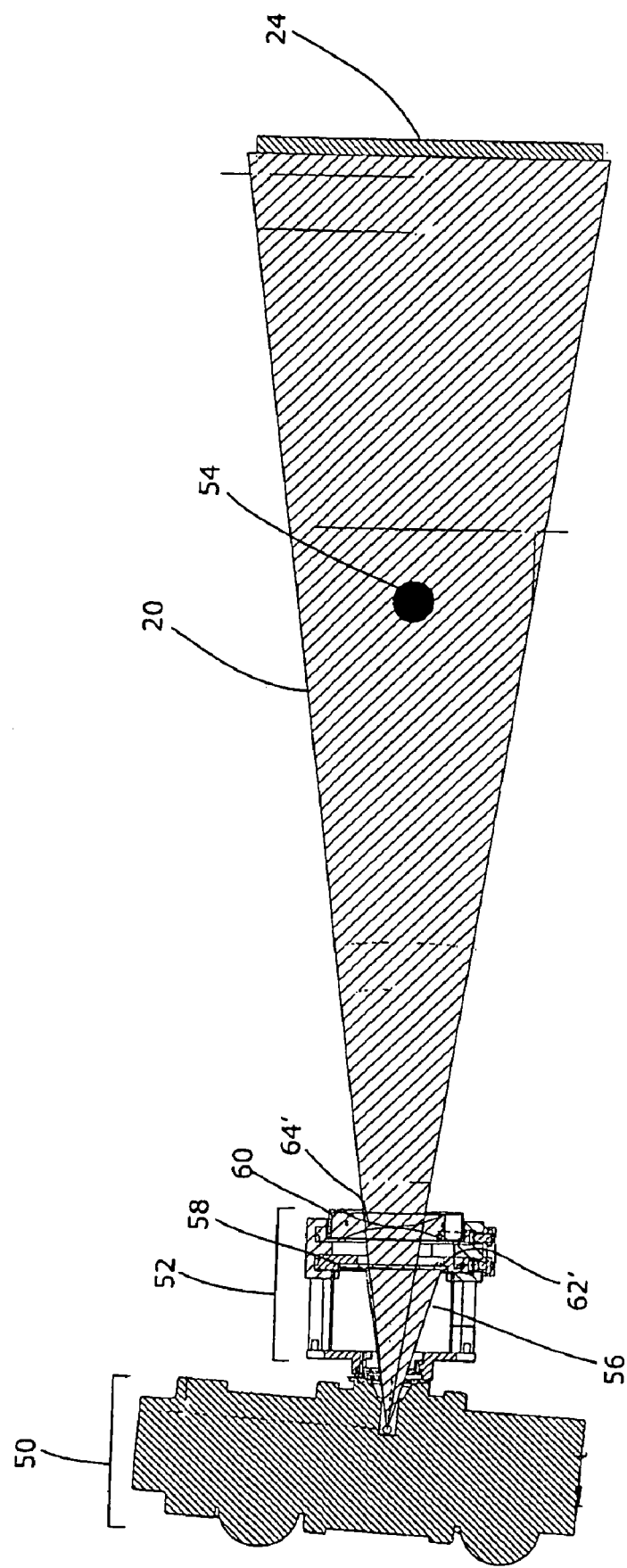
FIG. 6 shows the apparatus of FIG. 5 in a second collimation.

FIG. 6 shows the same apparatus in which an alternative beam collimator 62' has been fitted, together with an alternative filter 64'. The second filter 64' differs only in that its centre is suitably offset. The alternative beam collimator 62' differs in that it collimates the beam asymmetrically with respect to the beam 56 emanating from the X-ray source 50, but nevertheless symmetrically about the beam axis 22 and the isocentre 54. In this way, the apparatus can be used as described with respect to FIG. 1.

Figure 7:
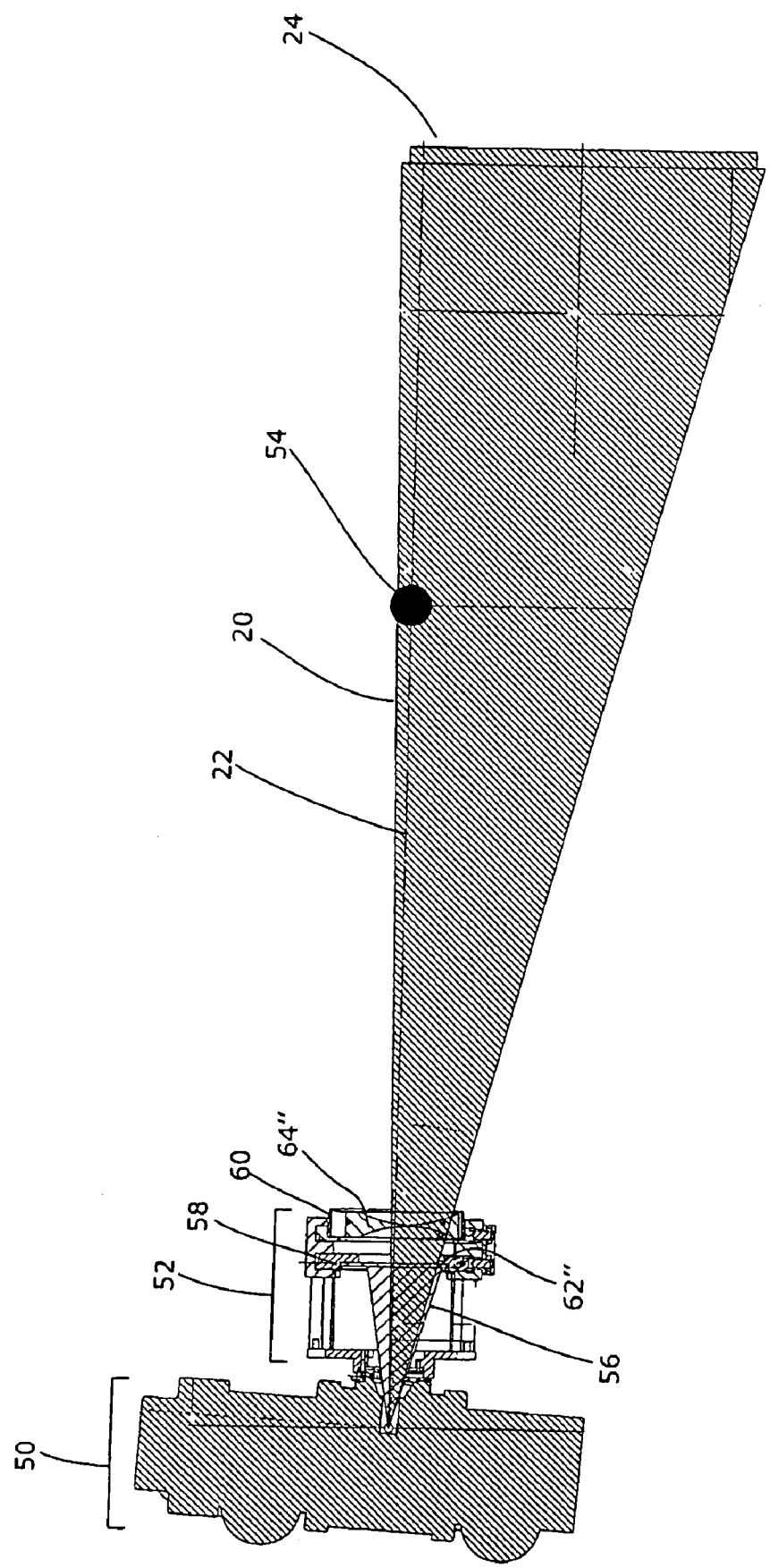
FIG. 7 shows the apparatus of FIG. 5 in a third collimation.

FIG. 7 shows the same apparatus with a still further alternative collimator 62" and filter 64". In this case, the collimator 62" collimates the beam 56 asymmetrically, but this time in the opposite sense to that of FIG. 6. Instead of returning the beam towards the isocentre 54, the beam is offset still further from the isocentre 54 such that the beam 20 only just overlaps with the isocentre 54. This produces an offset beam for use in the manner as described with respect to FIG. 2 above.

It will be appreciated that the two extremities of collimation that are required in clinical practice, as shown in FIG. 6 and FIG. 7 respectively, now occupy the extremities of the usable area of the beam. The fullest available extent 56 of the beam is therefore used, by virtue of the angle 66 between the X-ray source 50 and the collimator set 52.

This relieves the designer of the need to select an X-ray tube on the basis of its wide available field, and allows the optimisation of the X-ray tube based on other requirements of the device.

Figure 8:
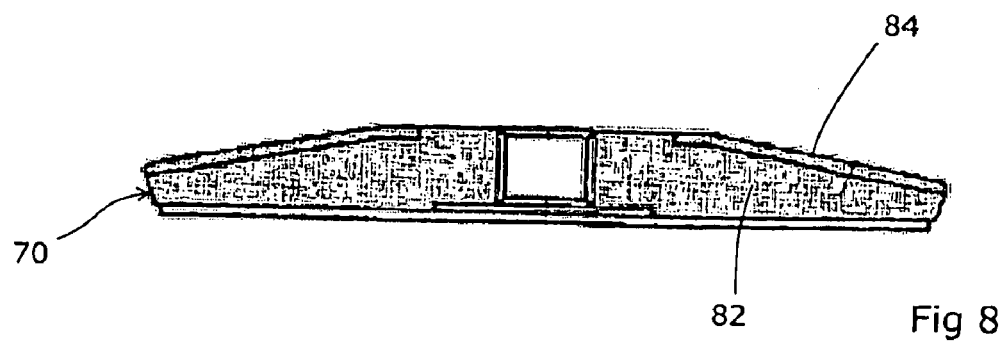
FIG. 8 shows a typical anode for investigative X-ray apparatus.
Figure 9:
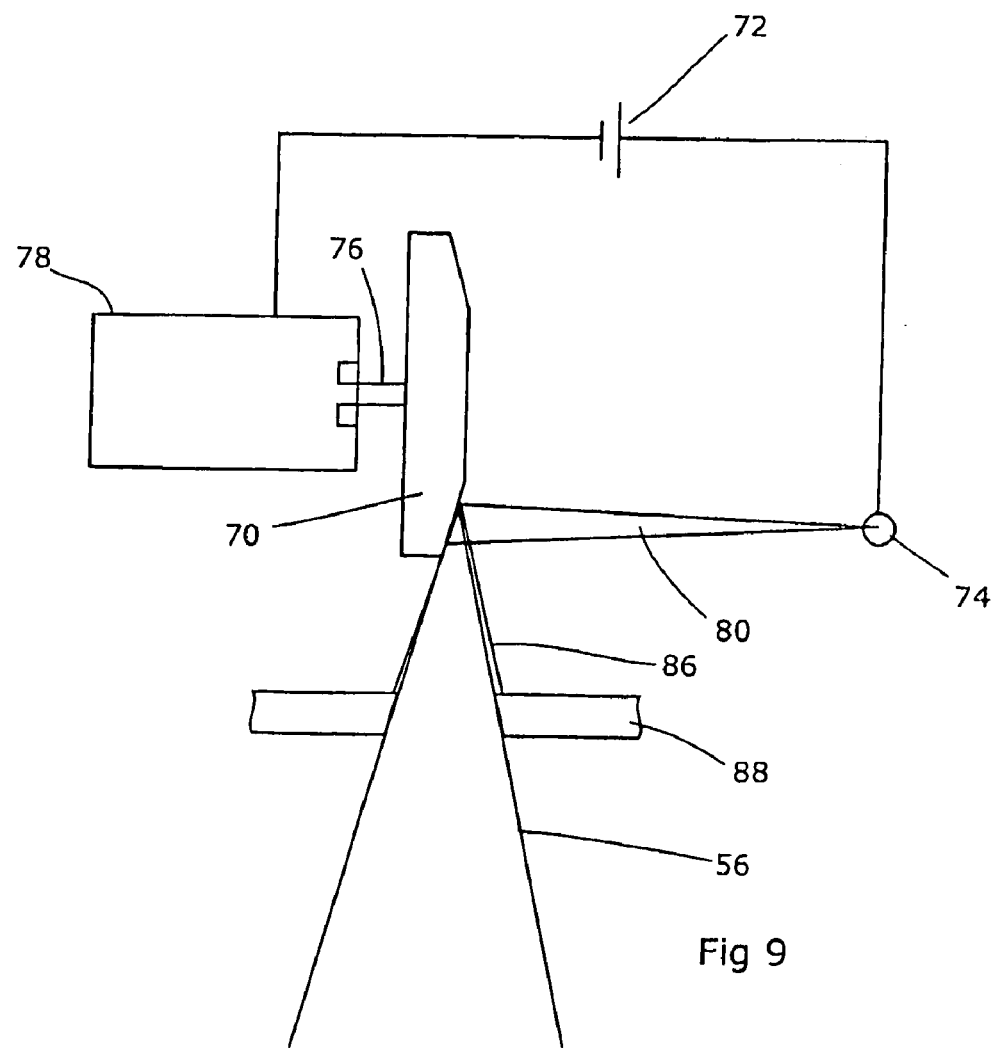
FIG. 9 shows the X-ray tube schematically.

FIG. 8 shows, for information, a typical target 70 for use in an X-ray source 50. FIG. 9 shows the apparatus, schematically, including the target 70. A high voltage source 72, typically providing 150 kV is arranged to produce a potential between a hot filament 74 and the anode 70. The anode 70 is itself mounted on a spindle 76 which is rotatable by a motor 78. Thus, a beam of electrons 80 travels from the filament 74 towards the anode 70. The anode 70 has a molybdenum core 82 with a generally circular face on which is mounted an annular ring 84 of tungsten/rhenium target material. The apparatus is disposed such that the electron beam 80 lands on the anode at the target material 84. The surface is slightly bevelled so that, in respect of the surface, the electron beam 80 arrives at an angle and, as a result, an emitted beam of X-rays 86 departs the anode 70 in a direction which is roughly perpendicular to the incoming electron beam 80. This beam 86 is then collimated by suitable beam stops 88 to produce the output beam 56 of the X-ray source.

The motor 78 drives the anode 70 via the spindle 76 so that the annular target 84 is constantly rotating. As a result, the point of contact of the incoming electron beam 80 is constantly moving across the anode although the rotationally symmetric design of the anode 70 means that this does not affect the output beam 56. As a result, the anode 70 is better able to cool notwithstanding the energy absorbed from the electron beam 80.

The entire apparatus of FIG. 9 is typically enclosed within a suitable vacuum flask, which is itself suspended in a bath of flowing oil so as to assist in heat removal.

It will be appreciate from FIGS. 8 and 9 that it is only possible to widen the output beam 56 within limits. The width of the output beam 56 will in practice be limited by the size of the rotating anode 70 and by the geometry of the apparatus, for example of the direction of the electron beam 80, the degree to which the target surface 84 is bevelled, and the dimensions of the target surface 84. Limitations such as the need to rotate the anode 70 and the requirement that the anode be adequately cooled mean that there are limits to the available width of the beam 56. Beyond those available limits, the X-ray Intensity becomes less uniform as it eventually fades away to nothing, a phenomenon known as "tube heel".

Accordingly, the invention as described with respect to FIGS. 5, 6 and 7 allows the available extent of the X-ray beam to be used more efficiently, thereby relaxing the design requirements placed on this aspect of the X-ray tube and allowing it to be optimised in other respects.

It will of course be understood that many variations may be made to the above-described embodiment without departing from the scope of the present invention.

The invention claimed is:

1. The investigative X-ray apparatus, comprising a source of X-rays emitting a cone beam centred on a beam axis, a collimator to limit the extent of the beam, and a two-dimensional detector, the apparatus being mounted on a support which is rotatable about a rotation axis, the collimator having a first state in which the collimated beam is directed towards the rotation axis and the second state in which the collimated beam is offset from the rotation axis, the two-dimensional detector being movable accordingly, the beam axis being offset from the rotation axis by a lesser amount than the collimated beam in the second state.

2. The investigative X-ray apparatus according to claim 1 in which the X-ray source is offset such that its natural axis is halfway between the two extremes called for by the collimator.

3. The investigative X-ray apparatus according to claim 2 in which the X-ray source is fixedly located in its offset position.

4. The investigative X-ray apparatus according to claim 3 of the preceding claims, having an isocentre, in which the X-ray source is not directed towards the isocentre.

5. The radiotherapeutic apparatus comprising:
a therapeutic source of high energy radiation; and
an investigative X-ray apparatus according to claim 3.

6. The investigative X-ray apparatus according to claim 2 in which the offset is between 3 and 4°.

7. The investigative X-ray apparatus according to claim 6 of the preceding claims, having an isocentre, in which the X-ray source is not directed towards the isocentre.

8. The radiotherapeutic apparatus comprising:
a therapeutic source of high energy radiation; and
an investigative X-ray apparatus according to claim 6.

9. The investigative X-ray apparatus according to claim 2 of the preceding claims, having an isocentre, in which the X-ray source is not directed towards the isocentre.

10. The radiotherapeutic apparatus comprising:
a therapeutic source of high energy radiation; and
an investigative X-ray apparatus according to claim 2.

11. The investigative X-ray apparatus according to claim 1 having an isocentre, in which the X-ray source is not directed towards the isocentre.

12. The radiotherapeutic apparatus comprising:
a therapeutic source of high energy radiation; and
an investigative X-ray apparatus according to claim 11.

13. The radiotherapeutic apparatus comprising:
a therapeutic source of high energy radiation; and
an investigative X-ray apparatus according to claim 1.

* * * * *